United States Patent
Petrash et al.

(10) Patent No.: US 9,701,713 B2
(45) Date of Patent: Jul. 11, 2017

(54) COMPOSITIONS AND METHODS FOR INTRODUCTION OF MACROMOLECULES INTO CELLS

(75) Inventors: Jonathan Mark Petrash, Englewood, CO (US); Niklaus Mueller, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 14/008,221

(22) PCT Filed: Mar. 30, 2012

(86) PCT No.: PCT/US2012/031372
§ 371 (c)(1),
(2), (4) Date: Nov. 26, 2013

(87) PCT Pub. No.: WO2012/135575
PCT Pub. Date: Oct. 4, 2012

(65) Prior Publication Data
US 2014/0235553 A1     Aug. 21, 2014

Related U.S. Application Data

(60) Provisional application No. 61/469,797, filed on Mar. 30, 2011.

(51) Int. Cl.
| | | |
|---|---|---|
| *A61K 38/00* | (2006.01) | |
| *C07K 7/00* | (2006.01) | |
| *C07K 7/08* | (2006.01) | |
| *C07K 14/47* | (2006.01) | |
| *A61K 47/48* | (2006.01) | |
| *C07K 14/005* | (2006.01) | |

(52) U.S. Cl.
CPC .......... *C07K 7/08* (2013.01); *A61K 47/48238* (2013.01); *A61K 47/48315* (2013.01); *C07K 14/005* (2013.01); *C07K 14/47* (2013.01); *A61K 38/00* (2013.01); *C07K 2319/10* (2013.01); *C07K 2319/35* (2013.01); *C12N 2710/16622* (2013.01)

(58) Field of Classification Search
None
See application file for complete search history.

(56) References Cited

U.S. PATENT DOCUMENTS

| | | | |
|---|---|---|---|
| 2003/0148983 A1 | 8/2003 | Fontoura et al. | |
| 2004/0157289 A1* | 8/2004 | Salerno et al. | 435/69.1 |
| 2004/0197347 A1* | 10/2004 | Sykes | A61K 39/245 424/186.1 |
| 2007/0190027 A1* | 8/2007 | Zhou et al. | 424/93.2 |
| 2009/0149384 A1 | 6/2009 | Rao et al. | |

OTHER PUBLICATIONS

International Search Report and Written Opinion for International (PCT) Patent Application No. PCT/US12/31372 mailed Aug. 10, 2012, 10 pages.
De Jong et al., Uniprot Accession No. P02489, 2005, 3 pages.
Trybala et al., "Structural and functional features of the polycationic peptide required for inhibition of herpes simplex virus invasion of cells," Antiviral Research, 2004, vol. 62, Iss. 3, pp. 125-134.
Wadia et al., "Transmembrane delivery of protein and peptide drugs by TAT-mediated transduction in the treatment of cancer," Advanced Drug Delivery Reviews, 2005, vol. 57, Iss. 4, pp. 579-596.
International Preliminary Report on Patentability for International (PCT) Patent Application No. PCT/US2012/031372 mailed Mar. 27, 2014, 8 pages.

* cited by examiner

*Primary Examiner* — Jeanette Lieb
(74) *Attorney, Agent, or Firm* — Sheridan Ross P.C.

(57) ABSTRACT

Disclosed are novel compositions and methods for introduction of macromolecules and nanoparticles into living cells. The invention includes a polypeptide sequence which when fused to a macromolecule or nanoparticle enhances its introduction into the cell.

14 Claims, 11 Drawing Sheets

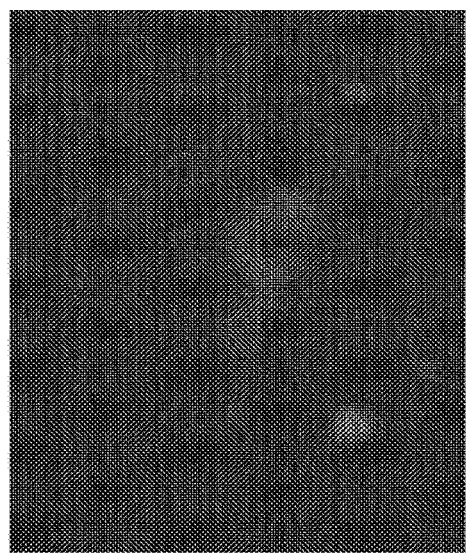
FIG 1A — Cells Treated with αB-crystallin
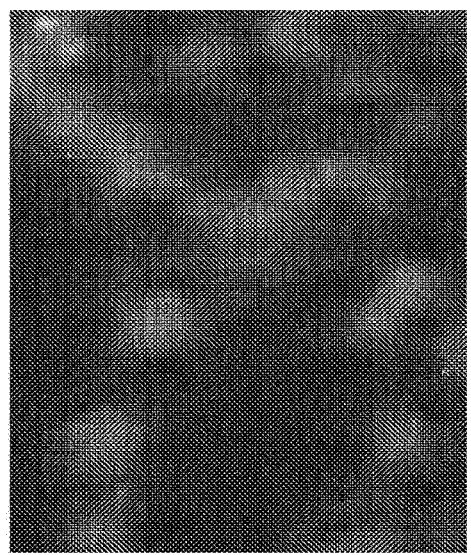
FIG 1B — Cells Treated with NTD-αB-crystallin

NTD Sequence

NH2-GSRVQIRCRFRNSTR-COOH

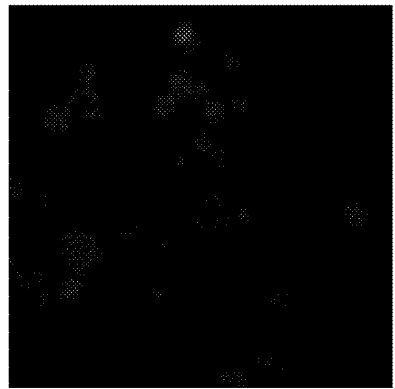
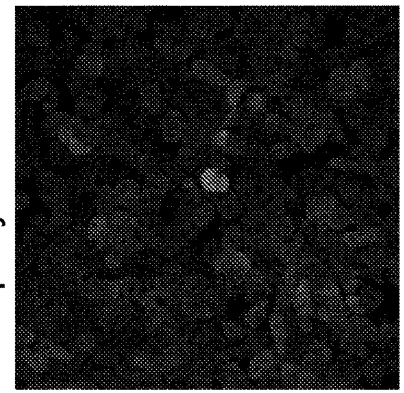
Figure 10

SEQUENCE LISTING

<160> NUMBER OF SEQ ID NOS: 5

<210> SEQ ID NO 1

```
<211> LENGTH: 15
<212> TYPE: PRT
<213> ORGANISM: Artificial Sequence
<220> FEATURE:
<223> OTHER INFORMATION: Synthetic

<400> SEQUENCE: 1

Gly Ser Arg Val Gln Ile Arg Cys Arg Phe Arg Asn Ser Thr Arg
1               5                   10                  15

<210> SEQ ID NO 2
<211> LENGTH: 188
<212> TYPE: PRT
<213> ORGANISM: Artificial Sequence
<220> FEATURE:
<223> OTHER INFORMATION: Synthetic

<400> SEQUENCE: 2

Met Gly Ser Arg Val Gln Ile Arg Cys Arg Phe Arg Asn Ser Thr Arg
1               5                   10                  15

Asp Val Thr Ile Gln His Pro Trp Phe Lys Arg Thr Leu Gly Pro Phe
            20                  25                  30

Tyr Pro Ser Arg Leu Phe Asp Gln Phe Phe Gly Glu Gly Leu Phe Glu
        35                  40                  45

Tyr Asp Leu Leu Pro Phe Leu Ser Ser Thr Ile Ser Pro Tyr Tyr Arg
    50                  55                  60

Gln Ser Leu Phe Arg Thr Val Leu Asp Ser Gly Ile Ser Glu Val Arg
65                  70                  75                  80

Ser Asp Arg Asp Lys Phe Val Ile Phe Leu Asp Val Lys His Phe Ser
                85                  90                  95

Pro Glu Asp Leu Thr Val Lys Val Gln Asp Asp Phe Val Glu Ile His
            100                 105                 110

Gly Lys His Asn Glu Arg Gln Asp Asp His Gly Tyr Ile Ser Arg Glu
        115                 120                 125

Phe His Arg Arg Tyr Arg Leu Pro Ser Asn Val Asp Gln Ser Ala Leu
    130                 135                 140

Ser Cys Ser Leu Ser Ala Asp Gly Met Leu Thr Phe Cys Gly Pro Lys
145                 150                 155                 160

Ile Gln Thr Gly Leu Asp Ala Thr His Ala Glu Arg Ala Ile Pro Val
                165                 170                 175

Ser Arg Glu Glu Lys Pro Thr Ser Ala Pro Ser Ser
            180                 185

<210> SEQ ID NO 3
<211> LENGTH: 567
<212> TYPE: DNA
<213> ORGANISM: Artificial Sequence
<220> FEATURE:
<223> OTHER INFORMATION: Synthetic

<400> SEQUENCE: 3
atgggatcac gagtgcaaat ccgatgtcga tttcgaaatt caacccgaga cgtgaccatc    60
cagcacccct ggttcaagcg caccctgggg cccttctacc ccagccggct gttcgaccag   120
tttttcggcg agggcctttt tgagtatgac ctgctgccct tcctgtcgtc caccatcagc   180
ccctactacc gccagtccct cttccgcacc gtgctggact ccggcatctc tgaggttcga   240
tccgaccggg acaagttcgt catcttcctc gatgtgaagc acttctcccc ggaggacctc   300
accgtgaagg tgcaggacga ctttgtggag atccacggaa agcacaacga gcgccaggac   360
```

| | |
|---|---|
| gaccacggct acatttcccg tgagttccac cgccgctacc gcctgccgtc caacgtggac | 420 |
| cagtcggccc tctcttgctc cctgtctgcc gatggcatgc tgaccttctg tggccccaag | 480 |
| atccagactg gcctggatgc cacccacgcc gagcgagcta tccccgtgtc gcgggaggag | 540 |
| aagcccacct cggctccctc gtcctaa | 567 |

<210> SEQ ID NO 4
<211> LENGTH: 190
<212> TYPE: PRT
<213> ORGANISM: Artificial Sequence
<220> FEATURE:
<223> OTHER INFORMATION: Synthetic

<400> SEQUENCE: 4

Met Gly Ser Arg Val Gln Ile Arg Cys Arg Phe Arg Asn Ser Thr Arg
1               5                   10                  15

Asp Ile Ala Ile His His Pro Trp Ile Arg Arg Pro Phe Phe Pro Phe
            20                  25                  30

His Ser Pro Ser Arg Leu Phe Asp Gln Phe Phe Gly Glu His Leu Leu
        35                  40                  45

Glu Ser Asp Leu Phe Pro Thr Ser Thr Ser Leu Ser Pro Phe Tyr Leu
    50                  55                  60

Arg Pro Pro Ser Phe Leu Arg Ala Pro Ser Trp Phe Asp Thr Gly Leu
65                  70                  75                  80

Ser Glu Met Arg Leu Glu Lys Asp Arg Phe Ser Val Asn Leu Asp Val
                85                  90                  95

Lys His Phe Ser Pro Glu Glu Leu Lys Val Lys Val Leu Gly Asp Val
            100                 105                 110

Ile Glu Val His Gly Lys His Glu Glu Arg Gln Asp Glu His Gly Phe
        115                 120                 125

Ile Ser Arg Glu Phe His Arg Lys Tyr Arg Ile Pro Ala Asp Val Asp
    130                 135                 140

Pro Leu Thr Ile Thr Ser Ser Leu Ser Ser Asp Gly Val Leu Thr Val
145                 150                 155                 160

Asn Gly Pro Arg Lys Gln Val Ser Gly Pro Glu Arg Thr Ile Pro Ile
                165                 170                 175

Thr Arg Glu Glu Lys Pro Ala Val Thr Ala Ala Pro Lys Lys
            180                 185                 190

<210> SEQ ID NO 5
<211> LENGTH: 573
<212> TYPE: DNA
<213> ORGANISM: Artificial Sequence
<220> FEATURE:
<223> OTHER INFORMATION: Synthetic

<400> SEQUENCE: 5

| | |
|---|---|
| atgggatcac gagtgcaaat ccgatgtcga tttcgaaatt caacccgaga catcgccatc | 60 |
| caccacccct ggatccgccg ccccttcttt cctttccact cccccagccg cctctttgac | 120 |
| cagttcttcg gagagcacct gttggagtct gatcttttcc cgacgtctac ttccctgagt | 180 |
| cccttctacc ttcggccacc ctccttcctg cgggcaccca gctggtttga cactggactc | 240 |
| tcagagatgc gcctggagaa ggacaggttc tctgtcaacc tggatgtgaa gcacttctcc | 300 |
| ccagaggaac tcaaagttaa ggtgttggga gatgtgattg aggtgcatgg aaaacatgaa | 360 |
| gagcgccagg atgaacatgg tttcatctcc agggagttcc acaggaaata ccggatccca | 420 |
| gctgatgtag accctctcac cattacttca tccctgtcat ctgatggggt cctcactgtg | 480 |

```
aatggaccaa ggaaacaggt ctctggccct gagcgcacca ttcccatcac ccgtgaagag    540
aagcctgctg tcaccgcagc ccccaagaaa tga                                 573
```

US 9,701,713 B2

COMPOSITIONS AND METHODS FOR INTRODUCTION OF MACROMOLECULES INTO CELLS

CROSS REFERENCE TO RELATED APPLICATIONS

This application is a national stage application under 35 U.S.C. 371 of PCT Application No. PCT/US2012/031372, having an international filing date of Mar. 30, 2012, which designated the United States, which PCT application claimed the benefit of priority under 35 U.S.C. §119(e) to U.S. Provisional Patent Application Ser. No. 61/469,797, filed Mar. 30, 2011, both of which are incorporated herein by reference.

GOVERNMENT INTEREST

This invention was made with government support under grant number EY020361 awarded by the National Institutes of Health. The government has certain rights in the invention.

FIELD OF THE INVENTION

The invention relates to the field of recombinant DNA technology involving use of a novel polypeptide tag for introduction of macromolecules into living cells.

BACKGROUND OF THE INVENTION

The ability to introduce macromolecules, such as proteins, nucleic acids, carbohydrates and lipids into living cells is a powerful tool for manipulating and examining biological processes, and has exciting therapeutic implications.

Introduction of nanoparticles into living cells is also a powerful biological tool with therapeutic potential. Nanoparticles are generally defined as particles that are 100 nm or smaller in diameter and are used, or being evaluated for use, in many fields including biomedical field. For example, Iron oxide nanoparticles can be used to improve MRI images of cancer tumors.

Currently a number of techniques are available for introduction of macromolecules and/or nanoparticles into living cells. These include induction of enhanced membrane permeability by use of $Ca^{2+}$ and temperature shock, use of surface binding agents such as polyethylene glycol (PEG), liposome mediated delivery and direct microinjection into cells. While microinjection procedures can give high efficiencies relative to delivery into the cell, they require single cell manipulations and therefore, are inappropriate for treating masses of cells and are generally tedious and difficult to employ. On the other hand, while the other protocols are generally simple, and allow treatment of large numbers of cells en masse, they tend to have very low efficiency.

Thus, there exists a need in the art for new and improved methods for introducing macromolecules and/or nanoparticles into living eukaryotic cells that are simple, efficient, and can target large number of cells. The present invention addresses this need.

SUMMARY OF THE INVENTION

One embodiment of the present invention includes a composition comprising a peptide comprising an amino acid sequence that is at least 80% identical to the sequence GSRVQIRCRFRNSTR (referred to herein as SEQ ID NO:1), and a macromolecule or a nanoparticle, in which the peptide is linked to the macromolecule or the nanoparticle and the peptide facilitates or enhances the introduction of the macromolecule or the nanoparticle into a cell.

Another embodiment of the present invention includes a method of treating or preventing a disease in an individual, comprising administering to the individual a composition comprising: a peptide comprising an amino acid sequence that is at least 80% identical to SEQ ID NO:1 (GSRVQIRCRFRNSTR), and a macromolecule or a nanoparticle, wherein the peptide is linked to the macromolecule or the nanoparticle; the peptide facilitates or enhances the introduction of the macromolecule of the nanoparticle into a cell, and wherein the macromolecule or nanoparticle provides a therapeutic benefit in the disease.

In some embodiments, the macromolecule may be a protein, carbohydrate, lipid, or nucleic acid. In some embodiments, the macromolecule is a protein. In some embodiments, the protein may be a small heat shock protein including without limitation HSPB1, HSPB2, HSPB3, HSPB4, HSPB5, HSPB6, HSPB7, HSPB8, HSPB9 or HSPB10. In some embodiments, the protein may be alpha crystallin. In some embodiments, the protein may be αA-crystallin or αB-crystallin. In some embodiments, the peptide may be linked to the N terminus of the protein. In some embodiments, the composition may comprise an amino acid sequence that is at least 80% identical to SEQ ID NO:2 or SEQ ID NO:4.

In some embodiments, the invention may comprise an isolated nucleic acid molecule comprising a nucleic acid sequence encoding the composition. In some embodiments, the invention may comprise a recombinant nucleic acid molecule comprising the isolated nucleic acid molecule.

In some embodiments, the composition of the present invention may further comprise a pharmaceutically acceptable carrier. In some embodiments, the invention may comprise a method of treating or preventing a disease in an individual, comprising administering to the individual the compositions of the present invention. In some embodiments, the invention may comprise the use of the compositions of the present invention in the preparation of a medicament for the treatment of a disease. In some embodiments, the disease may be an ocular disease, neurodegenerative disease, myopathy, asthma, or cancer. In some embodiments, the ocular disease may be cataract, retinitis pigmentosa, retinopathy, age-related macular degeneration, uveitis, trauma, or ischemia.

BRIEF DESCRIPTION OF THE DRAWINGS

FIGS. 1A and 1B are fluorescence microscopy images of lens-derived tissue culture cells incubated with fluorescently labeled protein αB-crystallin (or HSPB5) and NTD-αB-crystallin, respectively. A much stronger signal in cells incubated with NTD-αB-crystallin (FIG. 1B) indicates that the addition of the NTD markedly enhanced entry of –αB-crystallin into these cells.

FIG. 10 shows the efficacy of α crystallins in preventing protein aggregation and promoting protein stabilization using a cell culture model. Human gamma crystallin, either in its wild type form (γ-crystallin) or in an aggregation-prone mutant form (T5P γ-crystallin), was expressed as a fusion protein with green fluorescent protein (GFP). Strong fluorescence was observed in cells expressing the wild type γ-crystallin/GFP fusion protein; in contrast, cells expressing the T5P aggregation-prone mutant form of γ-crystallin/GFP fusion showed virtually no fluorescence. However, treatment of these cells with α crystallin prevented the loss of fluorescence to the T5P/GFP fusion protein.

DETAILED DESCRIPTION OF THE INVENTION

Figures 2A, 2B:
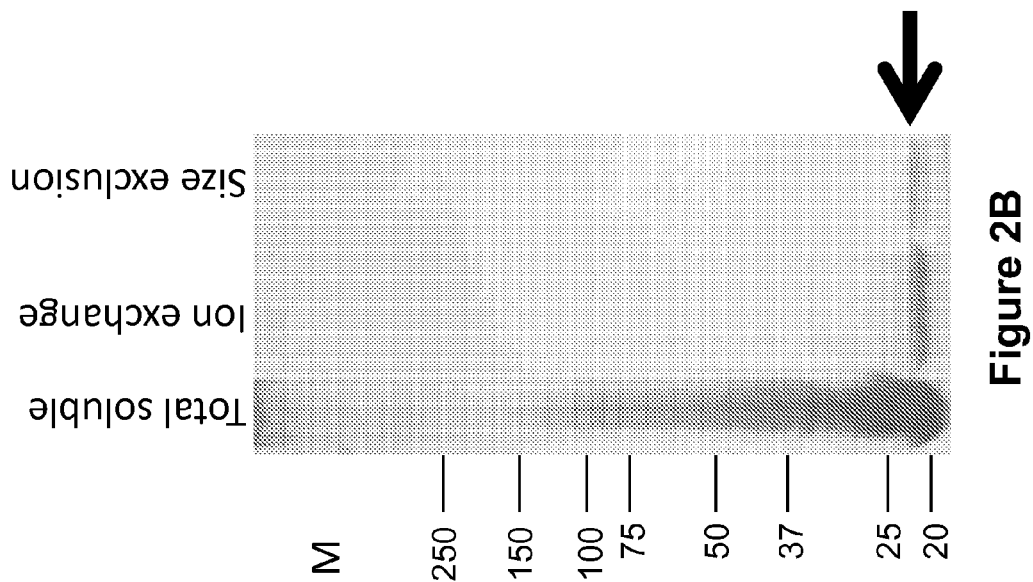
FIG. 2A shows the amino acid sequence of the Novel Trandsuction Domain.
FIG. 2B shows the SDS-PAGE with Coomassie blue staining demonstrating purification of the NTD-α crystallin fusion protein. Steps in the purification included cell extraction (total soluble) and separations using ion exchange and size exclusion chromatography media.

This invention generally relates to compositions and methods for introduction of macromolecules and nanoparticles into living cells. The invention includes the use of a peptide derived from a gene from herpes simplex virus type-1 which when fused to a macromolecule or a nanoparticle facilitates or enhances the entry of the macromolecule or nanoparticle into living cells. Heparin sulfate (HS) proteoglycan, a ubiquitous and multifunctional constituent of cell plasma membranes and extracellular matrices has been identified as a co-receptor for herpes simplex virus type 1 (HSV-1). Studies on peptides involved in cellular uptake of proteins have implicated heparin sulfate binding as a requirement for cellular uptake. Some studies have indicated that HSV-1 glycoprotein C (gC) is involved in binding to heparin sulfate, and that amino acids 137-151 (GSRVQIRCRFRNSTR; SEQ ID NO:1) of gC are the residues required for binding to heparin sulfate (Trybaka et al., J. of Gen. Virol. 75 743-752 1994). The present invention is based on the novel discovery that addition or linking of this peptide (termed herein as Novel Transduction Domain or "NTD") to a macromolecule, such as a protein, enhanced penetration of the macromolecule into cells. To the best of the present inventors' knowledge, there is no prior report of the use of this peptide to mediate introduction of a macromolecule into living cells and this is the first successful demonstration of such use.

Accordingly in one embodiment, the present invention includes a composition comprising a peptide that comprises an amino acid sequence comprising SEQ ID NO:1, that is linked to a macromolecule. The macromolecule may be a protein, carbohydrate, lipid, or a nucleic acid such as DNA or RNA.

In another embodiment the present invention includes a composition comprising a peptide that comprises an amino acid sequence comprising SEQ ID NO:1, that is linked to a nanoparticle. Nanoparticles are generally defined as particles that are 100 nm or smaller in diameter. The nanoparticle may be a nanomedicine formulation.

In some embodiments the macromolecule is a protein. Any protein known in the art may be used in the present invention. By way of example, in the present inventors used the NTD for delivery of alpha-crystallin into human lens-derived cells.

The crystallins are water-soluble structural proteins that occur in high concentration in the cytoplasm of eye lens cells. Four major groups of crystallin have been distinguished on the basis of size, charge and immunological properties: alpha-, beta- and gamma-crystallins occur in all vertebrate classes (though gamma-crystallins are low or absent in avian lenses); and delta-crystallin is found exclusively in reptiles and birds (de Jong et al., Trends Biochem. Sci. 14 365-8 1989; Simpson et al., Nat. Struct. Biol. 1 724-34 1994).

Alpha-crystallins are some of the most abundant soluble proteins in the lens and, along with the other lens crystallins, play an important role in establishing and maintaining the optical properties of the lens. Alpha crystallins occur as soluble large molecular weight complexes and comprise two subunits αA and αB each of which has a molecular weight of about 20 kD. Both αA and αB-crystallin form homo- as well as hetero-multimers of various sizes. αA and αB-crystallin have been isolated from a large number of organisms such as human, rat, mouse, cow and giant panda. Their sequences as well as those of the genes encoding them are known to those in the art and available at public databases such as Genbank. All such sequences are encompassed by the present invention. Human HSPB4 (mRNA) NM 000394, (protein) CAG28619.1 and Human HSPB5 (mRNA) NM_001885.1, (protein) NP_0018766.1.

Figure 3:
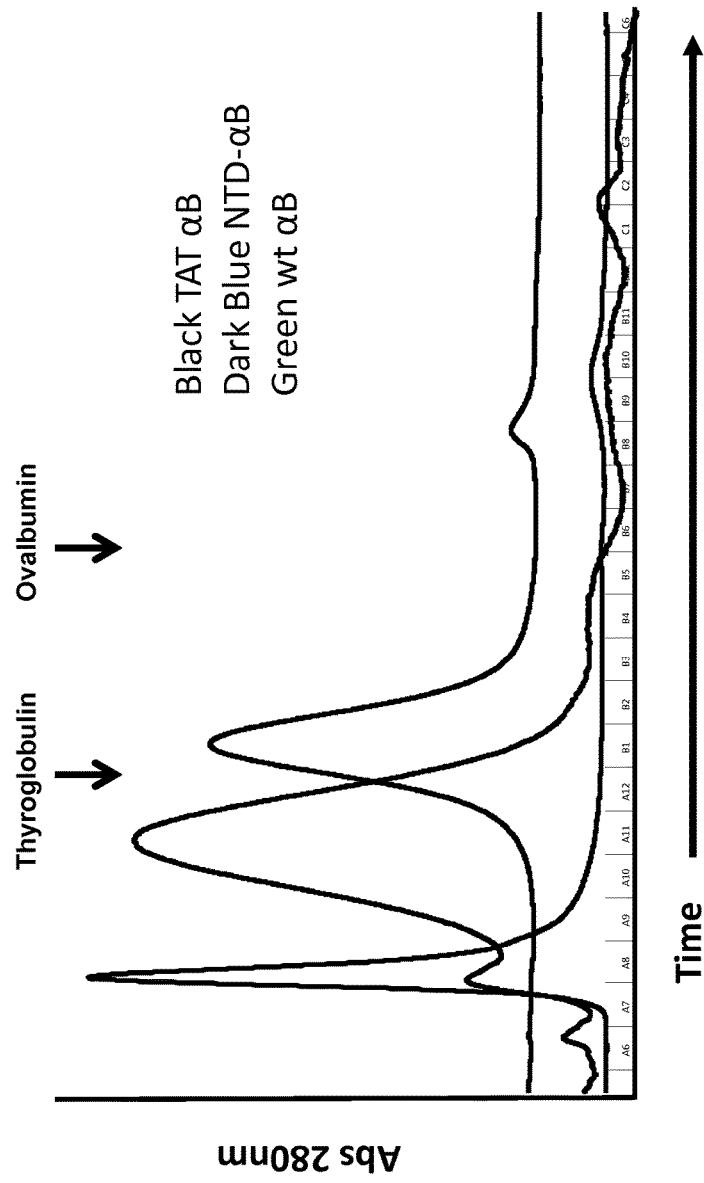
FIG. 3 shows that NTD-α crystallin retains the ability to form oligomeric complexes. The Size exclusion chromatography results (Superose 6 separation media) demonstrate formation of large oligomeric complexes. αB crystallin fused to the NTD peptide (dark blue trace) forms oligomeric complexes that appear to be larger than unfused αB crystallin (green) and smaller than αB crystallin fused to the TAT transduction peptide. Formation of oligomeric complexes is typical of small heat shock proteins, including the α crystallins, and is inherent to their ability to function as chaperone-like proteins.
Figure 4:
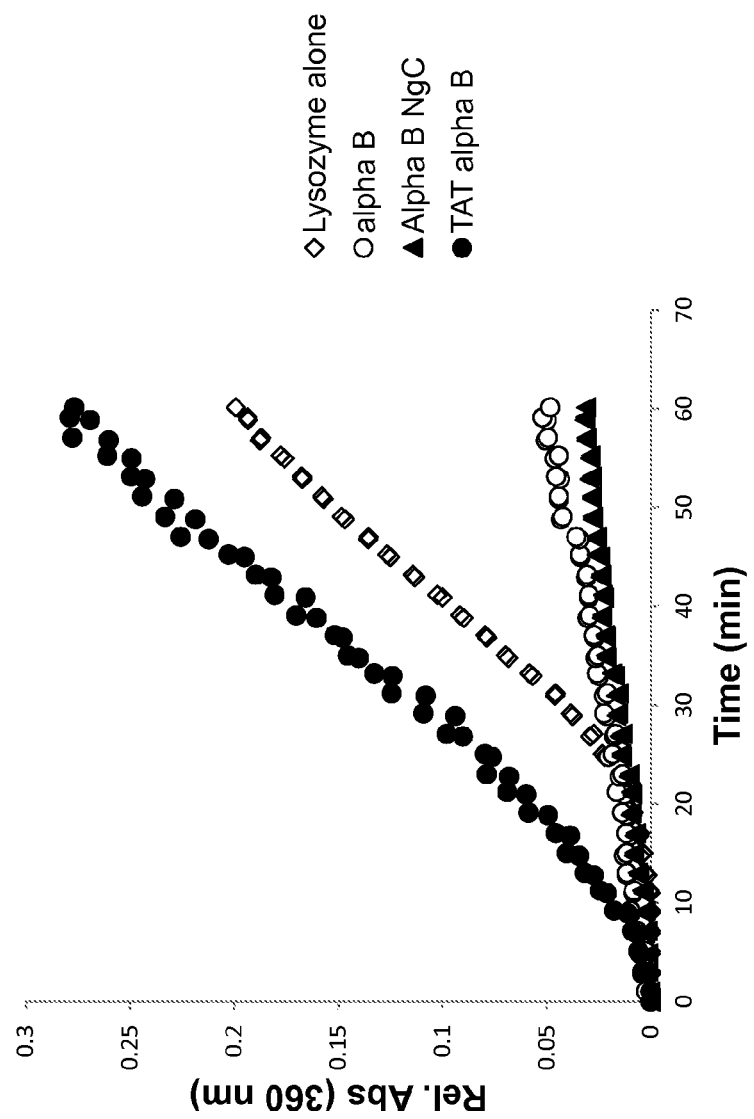
FIG. 4 shows the Chaperone-like activity profile of crystallin variants. The "Relative Absorbance (360 nm)" of lysozyme increases over time under assay conditions. The absorbance increase is an index of protein aggregation. A reduction in the slope of absorbance increase corresponds to inhibition of lysozyme aggregation. Data presented demonstrate that native αB crystallin and the NTD-αB crystallin fusion protein (referred in the figure as A B NgC) effectively suppress lysozyme aggregation; in contrast, the TAT-αB crystallin fusion protein does not suppress lysozyme aggregation.
Figure 5:
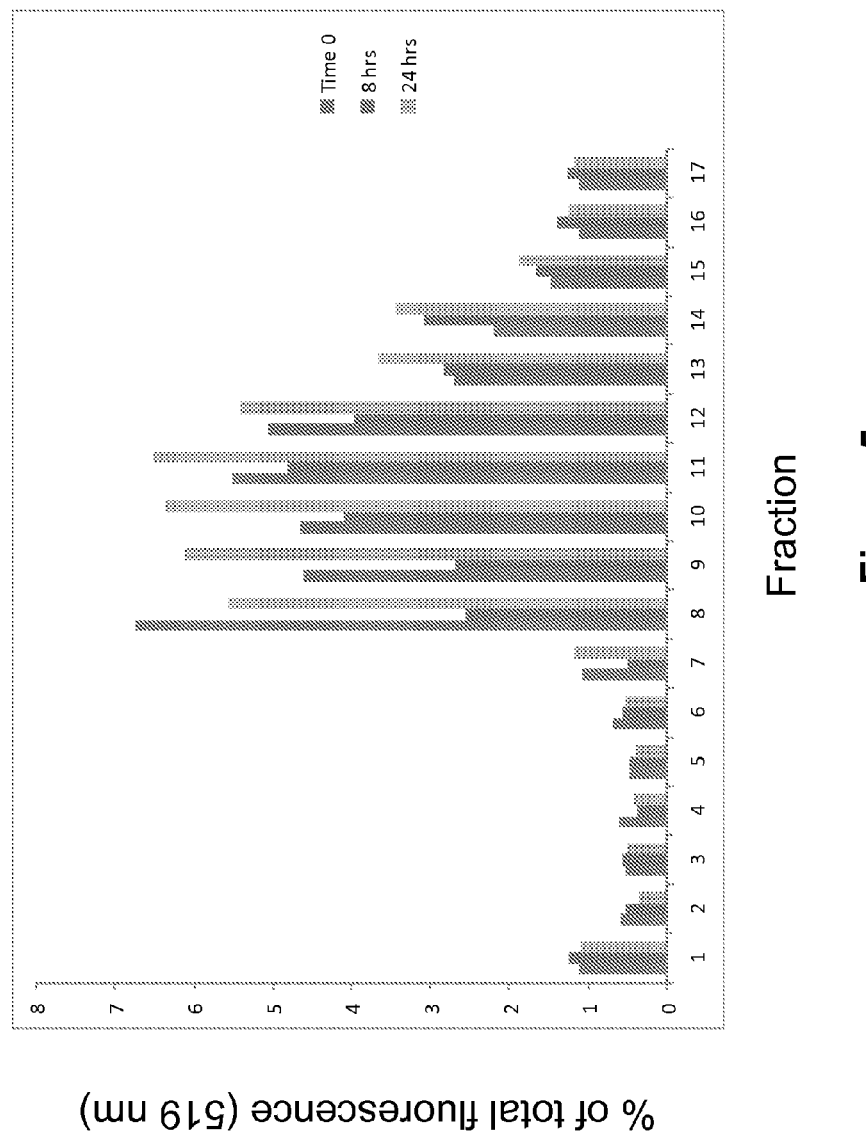
FIG. 5 shows that the NTD tagged crystallin shows "subunit exchange" and gets incorporated into oligomeric complexes. NTD-αB crystallin was covalently labeled with a small molecular weight fluorescent tag (AlexaFluor) and combined with a 10-fold molar excess of unlabeled αB crystallin (no transduction peptide). The protein was then incubated at 37° C. At various times after mixing, a quantity of protein mixture was removed and injected into a size exclusion FPLC separation column. Effluent material was assayed for the presence of the NTD-αB crystallin by measuring fluorescence. At time zero (blue data bars), the highest fluorescence signal appeared in the effluent at fraction 8. Analysis of the material after 8 hours (red data bars) and 24 hours (green data bars) of incubation showed the peak fluorescence shifted to fraction 11, indicating that the fluorescently-labeled fusion protein had become incorporated into oligomeric complexes that were of the native size for αB-crystallin. This process of incorporation into other oligomeric complexes (subunit exchange) is inherent to native α crystallin and is necessary in the mechanism behind chaperone-like suppression of protein aggregation.

As explained in Examples 1 and 2, fusion proteins comprising NTD linked to the N-terminus or C-terminus of αA-crystallin and αB-crystallin were constructed. SEQ ID NO. 2 denotes the amino acid sequence of the fusion protein containing NTD linked to the N terminus of the αA-crystallin protein and SEQ ID NO. 3 denotes the nucleic acid sequence encoding the same. SEQ ID NO. 4 denotes the amino acid sequence of the fusion protein containing NTD linked to the N terminus of the αB-crystallin protein and SEQ ID NO. 4 denotes the nucleic acid sequence encoding the same. Surprisingly, fusion proteins comprising NTD linked to the N-terminal of αA-crystallin and αB-crystallin proteins were soluble while the C-terminal tagged proteins were insoluble. Analysis of purified NTD-αB crystallin indicated that it retains the ability to form oligomeric complexes similar to wild type αB crystallin (see FIGS. 3 and 5). Further analysis showed that NTD-αB crystallin also retains the ability to prevent protein aggregation i.e. chaperon-like-activity (CLA) (see FIG. 4). These functional studies demonstrated that modification of human alpha crystallin by addition of the NTD peptide at the amino terminus does not substantially disrupt the structural integrity of the protein, nor does it substantially alter its biological activity as a chaperone-like protein.

Figure 6:
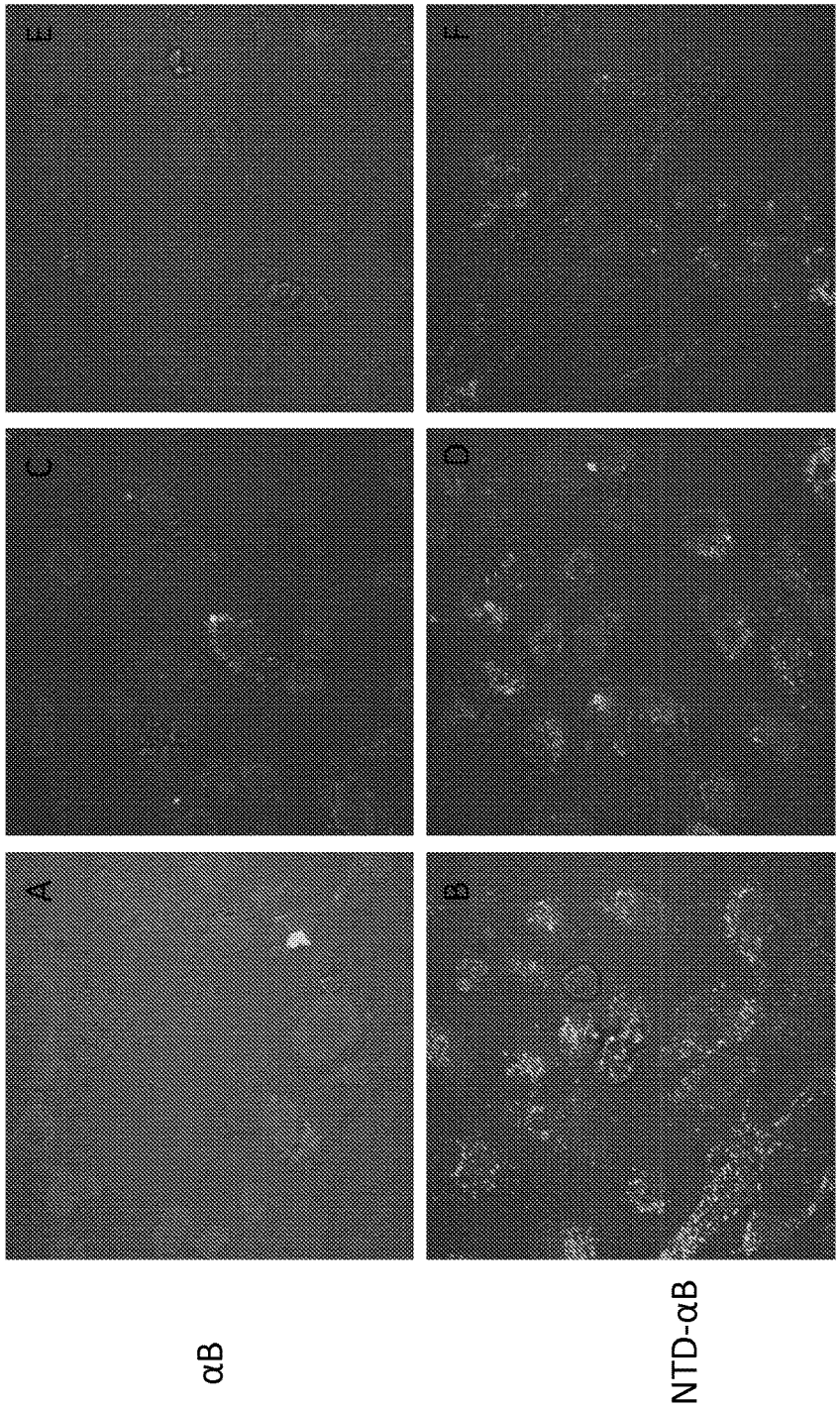
FIG. 6 presents fluorescence images of tissue culture cells transfected with fluorescently labeled αB crystallin and NTD-αB crystallin. The data shows that NTD-αB crystallin has higher cell penetration and retention than αB crystallin.

Since in vitro properties of alpha crystallin were unaffected by the addition of the NTD peptide, the ability of the NTD tag to enhance uptake of client proteins into living cells was investigated. To monitor cell uptake, wild type and NTD tagged crystallins were labeled with Alexa Fluor 488, a small reporter molecule. Equal amounts of protein were added to separate tissue culture plates containing human lens epithelial cells (HLE B3) and analyzed for their uptake into cells. At various times after addition of the protein to the cell media, cells were fixed and analyzed by fluorescent microscopy for cellular uptake of the labeled proteins. Results showed a dramatic difference conferred by the NTD peptide tag. Strong fluorescence was observed in cells exposed to the Alexa-conjugated NTD-αB protein. (See FIG. 1 and FIG. 6). In contrast, comparatively little intracellular fluorescence was observed in the control cells exposed to Alexa-conjugated αB protein (without the tag). These results demonstrated the utility of the NTD tag in facilitating uptake of a protein into target cells. Furthermore, the NTD tagged αB protein exhibited greater stability and cellular retention than the untagged αB protein. See FIGS. 6 and 7, Example 3. Compared with another cell penetration peptide TAT, the NTD sequence was found to be more effective in facilitating uptake of αB protein. See FIGS. 8 and 9, Example 4.

While this demonstration was carried out with αA-crystallin and αB-crystallin, one skilled in the art will readily understand that the NTD tag will confer enhanced uptake of other biopharmaceutical compounds, including other proteins, nucleic acids and their derivatives, carbohydrates, lipids as well as, nanoparticles such as nanoscale carriers fabricated from carrier substrates such as PLGA.

Accordingly, in one embodiment, the present invention includes a composition comprising a NTD peptide comprising an amino acid sequence that is at least about 80% identical to SEQ ID NO:1, wherein the NTD peptide is linked to a macromolecule or a nanoparticle and the peptide facilitates or enhances the introduction of the macromolecule of the nanoparticle into a cell. In various embodiments, the peptide may comprise an amino acid sequence that is at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, and at least about 100% identical to SEQ ID NO:1.

The macromolecule may be a protein, carbohydrate, lipid, or a nucleic acid such as DNA or RNA. In some embodiments the protein may be αA-crystallin or αB-crystallin.

In preferred embodiments the peptide is linked to the N-terminus of the αA-crystallin or αB-crystallin.

In some embodiments, the composition comprises a fusion protein in which the NTD is linked to the N-terminus of the αA-crystallin protein. In such embodiments, the fusion protein may comprise an amino acid sequence that is at least about 80% identical to SEQ ID NO:2. In various embodiments, the fusion protein may comprise an amino acid sequence that is at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identical to SEQ ID NO:2.

In some embodiments, the composition comprises a fusion protein in which the NTD is linked to the N-terminus of the αB-crystallin protein. In such embodiments, the fusion protein may comprise an amino acid sequence that is at least about 80% identical to SEQ ID NO:4. In various embodiments, the fusion protein may comprise an amino acid sequence that is at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identical to SEQ ID NO:4.

In some embodiments the present invention includes an isolated nucleic acid molecule encoding the compositions of the present invention. Accordingly, in some embodiments the nucleic acid molecule encodes a fusion protein comprising the NTD peptide linked to a protein.

In some embodiments, the nucleic acid may encode a fusion protein in which the NTD peptide is linked to the N-terminus of the αA-crystallin. In such embodiments, the nucleic acid molecule may comprise a nucleotide sequence that is at least about 80% identical to SEQ ID NO:3. In various embodiments, the nucleic acid molecule may comprise a nucleotide sequence that is at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identical to SEQ ID NO:3.

In some embodiments, the nucleic acid may encode a fusion protein in which the NTD peptide is linked to the N-terminus of the αB-crystallin. In such embodiments, the nucleic acid molecule may comprise a nucleotide sequence that is at least about 80% identical to SEQ ID NO:5. In various embodiments, the nucleic acid molecule may comprise a nucleotide sequence that is at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identical to SEQ ID NO:5.

As used herein, an "isolated" nucleic acid molecule or nucleic acid sequence, is a nucleic acid molecule or sequence that has been removed from its natural milieu. As such, "isolated" does not necessarily reflect the extent to which the nucleic acid molecule has been purified. An isolated nucleic acid molecule includes DNA, RNA, or derivatives of either DNA or RNA, and can be double stranded or single stranded.

In some embodiments the present invention includes a recombinant nucleic acid molecule comprising the isolated nucleic acid molecule. In particular, recombinant molecules of the present invention include nucleic acid molecules that are operatively linked to one or more transcription control sequences. The phrase "operatively linked" refers to linking a nucleic acid molecule to a transcription control sequence in a manner such that the molecule is able to be expressed when transfected (i.e., transformed, transduced or transfected) into a host cell. Transcription control sequences, which can control the amount of protein produced, include sequences which control the initiation, elongation, and termination of transcription. Particularly important transcription control sequences are those which control transcription initiation, such as promoter and upstream activation sequences.

In some embodiments the composition further comprises a pharmaceutically acceptable carrier. As used herein, a pharmaceutically acceptable carrier refers to any substance or vehicle suitable for delivering the compositions of the present invention to a suitable in vivo or ex vivo site. Such a carrier can include, but is not limited to, an adjuvant, an excipient, or any other type of delivery vehicle or carrier.

In some embodiments, the present invention includes a method of treating or preventing a disease in an individual, comprising administering to the individual the compositions of the present invention comprising NTD peptide linked to a macromolecule or nanoparticle that may have a therapeutic effect in that disease.

Figure 11:
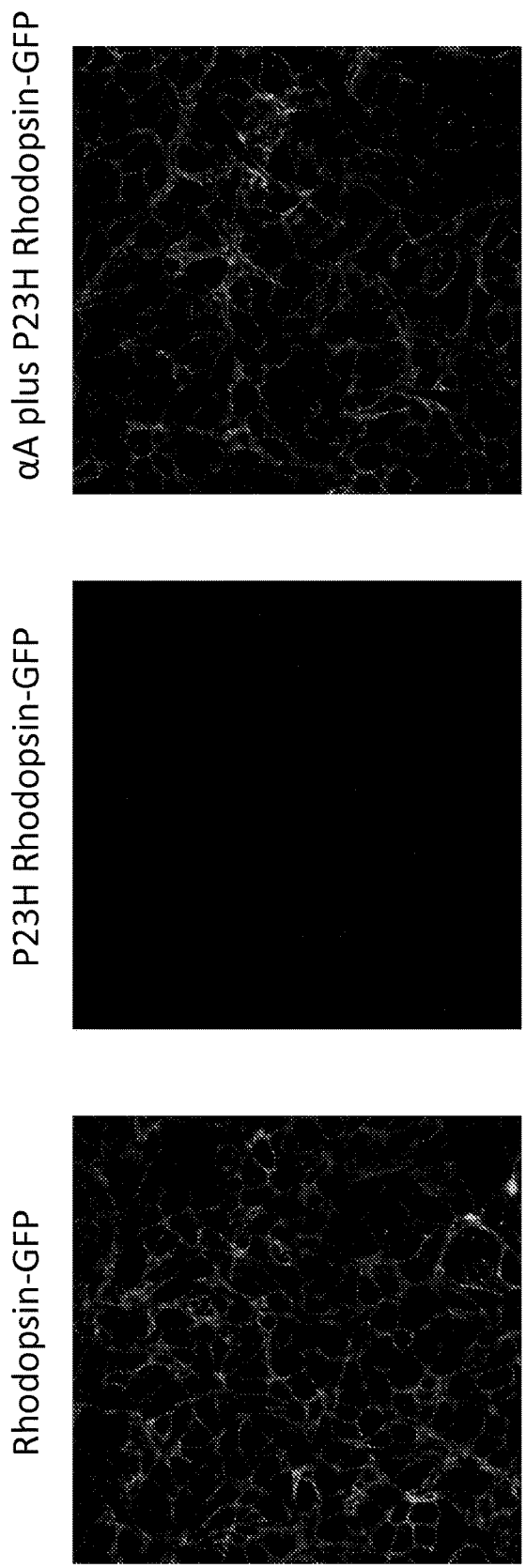
FIG. 11 shows efficacy of α crystallins in preventing protein aggregation and promoting stabilization of the protein rhodopsin. As shown, α crystallin prevents aggregation of the aggregation-prone mutant of rhodpsin, P23H rhodopsin.

For instance, alpha crystallins are known to prevent protein aggregation and possess 'chaperone like activity' (CLA). (See FIGS. 10 and 11 showing that αA crystallin is able to prevent aggregation of an aggregation-prone mutant form of gamma-crystallin (T5P g-crystallin), as well as rhodopsin (P23H rhodopsin)). Thus, they prevent the precipitation of denatured proteins and increase cellular tolerance to stress. It has been suggested that these functions are important for the maintenance of lens transparency and the prevention of cataracts. This is further supported by the observation that alpha crystallin mutations show an association with cataract formation. (Augusteyn R C, Clin Exp Optom, 87 356-66 2004). Alpha crystallin is also found at lower concentrations in nearly all tissues of the body, with αB-crystallin by far the more prevalent (Bhat & Nagineni, 1989; Kato et al. 1991). αB-crystallin is implicated in pathologies such as cataracts, neurodegenerative diseases, myopathies, asthma, and cancers. (Arrigo et al., FEBS Lett. 581(19) 3665-74 2007).

Accordingly, in another embodiment the present invention includes a method of treating or preventing an ocular disease, neurodegenerative disease, myopathy, asthma, or cancer in an individual, comprising administering to the individual the compositions of the present invention comprising NTD-αB crystallin and/or NTD-αA-crystallin. Examples of ocular disease may include cataract, retinitis pigmentosa, retinopathy, age-related macular degeneration, uveitis, trauma and ischemia. (Fort and Lampi, Experimental Eye Research (November 2010)).

Cataract is a protein aggregation disease of the lens. α-crystallin prevents protein aggregation and loss of native α-crystallin is associated with increased risk of cataract development. Introduction of additional α-crystallin protein into cells will lead to suppressed protein aggregation and help in treatment or prevention of cataract. Accordingly, in one embodiment the present invention includes a method of treating or preventing cataract in an individual, comprising administering to the individual the compositions of the present invention comprising NTD-αA and NTD-αB crystallin. Retinitis pigmentosa is a disease of the retina that involves an aggregation prone mutant of the protein rhodopsin. The P23H mutation within the rhodopsin gene (RHO) causes rhodopsin misfolding, endoplasmic reticulum (ER) stress, and activates the unfolded protein response (UPR), leading to rod photoreceptor degeneration and autosomal dominant retinitis pigmentosa. As shown in FIG. 11, α-A crystallin prevents P23H rhodopsin aggregation. Accordingly, in one embodiment the present invention includes a method of treating or preventing retinitis pigmentosa in an individual, comprising administering to the individual the compositions of the present invention comprising NTD-αA and NTD-αB crystallin. The term, "disease" refers to any deviation from the normal health of a mammal and includes a state when disease symptoms are present, as well as conditions in which a deviation (e.g., infection, gene mutation, genetic defect, etc.) has occurred, but symptoms are not yet manifested.

Treat," "treating" or "treatment" is used herein to mean to reduce (wholly or partially) the symptoms, duration or severity of a disease or condition, including curing the disease, or to prevent the disease or condition. Further, as used herein, "treatment" also refers to clinical intervention in an attempt to alter the natural course of the individual or cell being treated, and may be performed either for prophylaxis and/or during the course of clinical pathology. Desirable effects include preventing occurrence or recurrence of disease, alleviation of symptoms, diminishment of any direct or indirect pathological consequences of the disease, preventing metastasis, lowering the rate of disease progression, amelioration or palliation of the disease state, and remission or improved prognosis. Accordingly, a therapeutic benefit is not necessarily a cure for a particular disease or condition, but rather, preferably encompasses a result which most typically includes alleviation of the disease or condition, elimination of the disease or condition, reduction of a symptom associated with the disease or condition, prevention or alleviation of a secondary disease or condition resulting from the occurrence of a primary disease or condition (e.g., metastatic tumor growth resulting from a primary cancer), and/or prevention of the disease or condition.

In the case of cancer, the method of the invention preferably increases the death of tumor cells, decreases the invasive potential of tumor cells, increases the survival of an individual with cancer, and/or increases tumor regression, decreases tumor growth, and/or decreases tumor burden in the individual.

According to the present invention, the methods and assays disclosed herein are suitable for use in or with regard to an individual that is a member of the Vertebrate class, Mammalia, including, without limitation, primates, livestock and domestic pets (e.g., a companion animal). Most typically, a patient will be a human patient. According to the present invention, the terms "patient", "individual" and "subject" can be used interchangeably, and do not necessarily refer to an animal or person who is ill or sick (i.e., the terms can reference a healthy individual or an individual who is not experiencing any symptoms of a disease or condition).

According to the present invention, an effective administration protocol (i.e., administering a therapeutic composition in an effective manner) comprises suitable dose parameters and modes of administration that result in elicitation of an appropriate response in an animal that has a disease or condition, or that is at risk of contracting a disease or condition, preferably so that the animal is protected from the disease. A beneficial effect can easily be assessed by one of ordinary skill in the art and/or by a trained clinician who is treating the patient. Effective dose parameters can be determined using methods standard in the art for a particular disease. Such methods include, for example, determination of survival rates, side effects (i.e., toxicity) and progression or regression of disease. The preferred routes of administration will be apparent to those of skill in the art, depending on the type of condition to be prevented or treated, and/or the target cell population or tissue. Suitable route of administration, include oral, nasal, parenteral (e.g., intravenous, intraperitoneal, subcutaneous or intramuscular), transdermal, intraocular and topical (including buccally and sublingually). The preferred routes of administration for treatment of ocular diseases are oral, intraocular and topical.

The invention also includes pharmaceutical products comprising the compositions of the present invention suitable for treatment of the eye. Such pharmaceutical products include pharmaceutical compositions, devices and implants (which may be compositions or devices). Pharmaceutical formulations (compositions) for intraocular injection of a compound or compounds of the invention into the eyeball include solutions, emulsions, suspensions, particles, capsules, microspheres, liposomes, matrices, etc. See, e.g., U.S. Pat. No. 6,060,463, U.S. Patent Application Publication No. 2005/0101582, and PCT application WO 2004/043480, the complete disclosures of which are incorporated herein by reference. For instance, a pharmaceutical formulation for intraocular injection may comprise one or more compositions of the invention in combination with one or more pharmaceutically-acceptable sterile isotonic aqueous or non-aqueous solutions, suspensions or emulsions, which may contain antioxidants, buffers, suspending agents, thickening agents or viscosity-enhancing agents (such as a hyaluronic acid polymer).

Examples of suitable aqueous and nonaqueous carriers include water, saline (preferably 0.9%), dextrose in water (preferably 5%), buffers, dimethylsulfoxide, alcohols and polyols (such as glycerol, propylene glycol, polyethylene glycol, and the like). These compositions may also contain adjuvants such as wetting agents and emulsifying agents and dispersing agents. In addition, prolonged absorption of the injectable pharmaceutical form may be brought about by the inclusion of agents which delay absorption such as polymers and gelatin. Injectable depot forms can be made by incorporating the drug into microcapsules or microspheres made of biodegradable polymers such as polylactide-polyglycolide. Examples of other biodegradable polymers include poly(orthoesters), poly(glycolic) acid, poly(lactic) acid, polycaprolactone and poly(anhydrides). Depot injectable formulations are also prepared by entrapping the drug in liposomes (composed of the usual ingredients, such as dipalmitoyl phosphatidylcholine) or microemulsions which are compatible with eye tissue. Depending on the ratio of drug to polymer or lipid, the nature of the particular polymer or lipid components, the type of liposome employed, and whether the microcapsules or microspheres are coated or uncoated, the rate of drug release from microcapsules, microspheres and liposomes can be controlled. The compounds of the invention can also be administered surgically as an ocular implant. For instance, a reservoir container having a diffusible wall of polyvinyl alcohol or polyvinyl acetate and containing a compound or compounds of the invention can be implanted in or on the sclera. As another example, a composition of the invention can be incorporated into a polymeric matrix made of a polymer, such as polycaprolactone, poly(glycolic) acid, poly(lactic) acid, poly(anhydride), or a lipid, such as sebacic acid, and may be implanted on the sclera or in the eye. This is usually accomplished with the animal receiving a topical or local anesthetic and using a small incision made behind the cornea. The matrix is then inserted through the incision and sutured to the sclera.

Another embodiment of the invention is local topical administration of the compounds of the invention to the eye, and a particularly preferred embodiment of the invention is a topical pharmaceutical composition suitable for application to the eye. Topical pharmaceutical compositions suitable for application to the eye include solutions, suspensions, dispersions, drops, gels, hydrogels and ointments. Topical formulations suitable for application to the eye comprise one or more compounds of the invention in an aqueous or nonaqueous base. The topical formulations can also include absorption enhancers, permeation enhancers, thickening agents, viscosity enhancers, agents for adjusting and/or maintaining the pH, agents to adjust the osmotic pressure, preservatives, surfactants, buffers, salts (preferably sodium chloride), suspending agents, dispersing agents, solubilizing agents, stabilizers and/or tonicity agents. Topical formulations suitable for application to the eye will preferably comprise an absorption or permeation enhancer to promote absorption or permeation of the compound or compounds of the invention into the eye and/or a thickening agent or viscosity enhancer that is capable of increasing the residence time of a compound or compounds of the invention in the eye. Exemplary absorption/permeation enhancers include methysulfonylmethane, alone or in combination with dimethylsulfoxide, carboxylic acids and surfactants. Exemplary thickening agents and viscosity enhancers include dextrans, polyethylene glycols, polyvinylpyrrolidone, polysaccharide gels, Gelrite®, cellulosic polymers (such as hydroxypropyl methylcellulose), carboxyl-containing polymers (such as polymers or copolymers of acrylic acid), polyvinyl alcohol and hyaluronic acid or a salt thereof.

Liquid dosage forms (e.g., solutions, suspensions, dispersions and drops) suitable for treatment of the eye can be prepared, for example, by dissolving, dispersing, suspending, etc. a compound or compounds of the invention in a vehicle, such as, for example, water, saline, aqueous dextrose, glycerol, ethanol and the like, to form a solution, dispersion or suspension. If desired, the pharmaceutical formulation may also contain minor amounts of non-toxic auxillary substances, such as wetting or emulsifying agents, pH buffering agents and the like, for example sodium acetate, sorbitan monolaurate, triethanolamine sodium acetate, triethanolamine oleate, etc.

Aqueous solutions and suspensions suitable for treatment of the eye can include, in addition to a compound or compounds of the invention, preservatives, surfactants, buffers, salts (preferably sodium chloride), tonicity agents and water. If suspensions are used, the particle sizes should be less than 10 μm to minimize eye irritation. If solutions or suspensions are used, the amount delivered to the eye should not exceed 50 μl to avoid excessive spillage from the eye.

Colloidal suspensions suitable for treatment of the eye are generally formed from microparticles (i.e., microspheres, nanospheres, microcapsules or nanocapsules, where microspheres and nanospheres are generally monolithic particles of a polymer matrix in which the formulation is trapped, adsorbed, or otherwise contained, while with microcapsules and nanocapsules the formulation is actually encapsulated). The upper limit for the size of these microparticles is about 5μ to about 10μ.

Ophthalmic ointments suitable for treatment of the eye include a compound or compounds of the invention in an appropriate base, such as mineral oil, liquid lanolin, white petrolatum, a combination of two or all three of the foregoing, or polyethylene-mineral oil gel. A preservative may optionally be included.

Ophthalmic gels suitable for treatment of the eye include a compound or compounds of the invention suspended in a hydrophilic base, such as Carpobol-940 or a combination of ethanol, water and propylene glycol (e.g., in a ratio of 40:40:20). A gelling agent, such as hydroxylethylcellulose, hydroxypropylcellulose, hydroxypropylmethylcellulose or ammoniated glycyrrhizinate, is used. A preservative and/or a tonicity agent may optionally be included.

Hydrogels suitable for treatment of the eye are formed by incorporation of a swellable, gel-forming polymer, such as those listed above as thickening agents or viscosity enhancers, except that a formulation referred to in the art as a "hydrogel" typically has a higher viscosity than a formulation referred to as a "thickened" solution or suspension. In contrast to such preformed hydrogels, a formulation may also be prepared so to form a hydrogel in situ following application to the eye. Such gels are liquid at room temperature but gel at higher temperatures (and thus are termed "thermoreversible" hydrogels), such as when placed in contact with body fluids. Biocompatible polymers that impart this property include acrylic acid polymers and copolymers, N-isopropylacrylamide derivatives and ABA block copolymers of ethylene oxide and propylene oxide (conventionally referred to as "poloxamers" and available under the PLURONIC® tradename from BASF-Wayndotte).

In some embodiments the dispersions are liposomal, in which case the formulation is enclosed within liposomes (microscopic vesicles composed of alternating aqueous compartments and lipid bilayers).

Eye drops can be formulated with an aqueous or non-aqueous base also comprising one or more dispersing agents, solubilizing agents or suspending agents. Drops can be delivered by means of a simple eye dropper-capped bottle or by means of a plastic bottle adapted to deliver liquid contents dropwise by means of a specially shaped closure. The compounds of the invention can also be applied topically by means of drug-impregnated solid carrier that is inserted into the eye. Drug release is generally effected by dissolution or bioerosion of the polymer, osmosis, or combinations thereof. Several matrix-type delivery systems can be used. Such systems include hydrophilic soft contact lenses impregnated or soaked with the desired compound of the invention, as well as biodegradable or soluble devices that need not be removed after placement in the eye. These soluble ocular inserts can be composed of any degradable substance that can be tolerated by the eye and that is compatible with the compound of the invention that is to be administered. Such substances include, but are not limited to, poly(vinyl alcohol), polymers and copolymers of polyacrylamide, ethylacrylate and vinylpyrrolidone, as well as cross-linked polypeptides or polysaccharides, such as chitin.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention. Additional objects, advantages, and novel features of this invention will become apparent to those skilled in the art upon examination of the following examples thereof, which are not intended to be limiting.

Each publication or patent cited herein is incorporated herein by reference in its entirety.

EXAMPLES

Example 1

This example illustrates that addition of the novel transduction domain ("NTD") to a protein enhances entry of the protein into cells.

αB-crystallin (or HSPB5), with and without the novel transduction domain ("NTD") having the sequence GSRVQ-IRCRFRNSTR (SEQ ID NO:1), was produced in recombinant form and fluorescently-labeled using Alexa-based dye. Lens-derived tissue culture cells were incubated with equivalent amounts of each of the proteins for 24 hours. Cells were then visualized by fluorescence microscopy. The intensity of fluorescence signal correlates with the amount of HSPB5 taken up by tissue culture cells.

The results are shown in FIGS. 1A and 1B. A much stronger fluorescence signal was obtained in cells incubated with NTD-HSPB5 (FIG. 1B) as compared with the control in which cells were incubated with HSPB5 alone, indicating that the presence of the NTD markedly enhanced entry of HSPB5 into these cells.

Example 2

This example illustrates that NTD tagged αA- and αB-crystallins at their N terminal were soluble, formed complexes similar to wild type α-crystallin, showed enhanced uptake as compared to wild type α-crystallins and displayed chaperone-like activity (CLA).

Recombinant human αA- and αB-crystallins were modified by addition of putative transduction sequences at their N- or C-termini. These proteins were expressed in *E. coli* and isolated to apparent homogeneity using previously published methods (Cobb et al. 2000). Purified proteins were analyzed by size exclusion chromatography to determine size heterogeneity. CLA was assessed by measuring the ability of candidate proteins to suppress chemically-induced aggregation of substrate protein lysozyme in the presence of dithiothreitol at 37° C.

Effects of different transduction sequences, including an Arginine-rich nonapeptide (ARN) and NTD, were examined. It was found that α-crystallin subunits expressed in *E. coli* were insoluble if they were fused to either transduction peptide at the C-terminus. Attempts to refold these proteins by dialysis following denaturant treatment were unsuccessful. In addition, when ARN was fused to the amino terminus of α-crystallin, it was recovered in low levels from *E. coli*. In contrast, α-crystallin subunits modified by addition of the NTD peptide at the N-terminus were soluble.

The NTD modified α-crystallin subunits formed large molecule weight complexes of ~650 kDa, similar to wild-type α-crystallins, based on size exclusion chromatography, and exhibited subunit exchange. See FIGS. 3 and 5. These proteins also displayed CLA, as evidenced by suppressing the chemically-induced aggregation of substrate proteins such as lysozyme. See FIG. 4.

Further, αA- and αB-crystallins with and without the NTD tag were fluorescently-labeled using the fluorescent reporter molecule Alexa Fluor 488, and were incubated with human lens epithelial cells (HLE B3) and human embryonic kidney cells (HEK293). Time-dependent uptake was measured by fluorescent microscopy. At various times after addition of the protein to the cell media, cells were fixed and analyzed by fluorescent microscopy for cellular uptake of the labeled proteins. Wild-type α-crystallin proteins resulted in limited protein uptake. In contrast, uptake was markedly improved by addition of the NTD peptide sequence.

Example 3

This example illustrates that NTD-tagged αB crystallin has greater cell penetration and retention compared to non tagged native protein, and that NTD-tagged αB crystallin is stable inside cells.

αB crystallin, with or without fusion to the NTD peptide, was labeled with the small molecular weight fluorescent molecule AlexaFluor. It was then combined with tissue culture nutrient media and applied to a culture plate containing human lens cells. After 60 minutes, the culture media were removed, and replaced with culture media without crystallins. Entry and distribution of crystallins was measured over 3 days by observing fluorescence (green). Cell nuclei were stained with Hoechst dye (blue). Data showed that a quantity of αB crystallin without the NTD peptide gains entry to cells, but is substantially lost after 48 hours and is virtually undetectable after 72 hours. In contrast, αB crystallin fused to the NTD peptide is present at substantially higher levels at all three days of examination. See FIG. 6. This shows that addition of the NTD peptide to α B crystallin improves cell penetration and retention.

Figure 7:
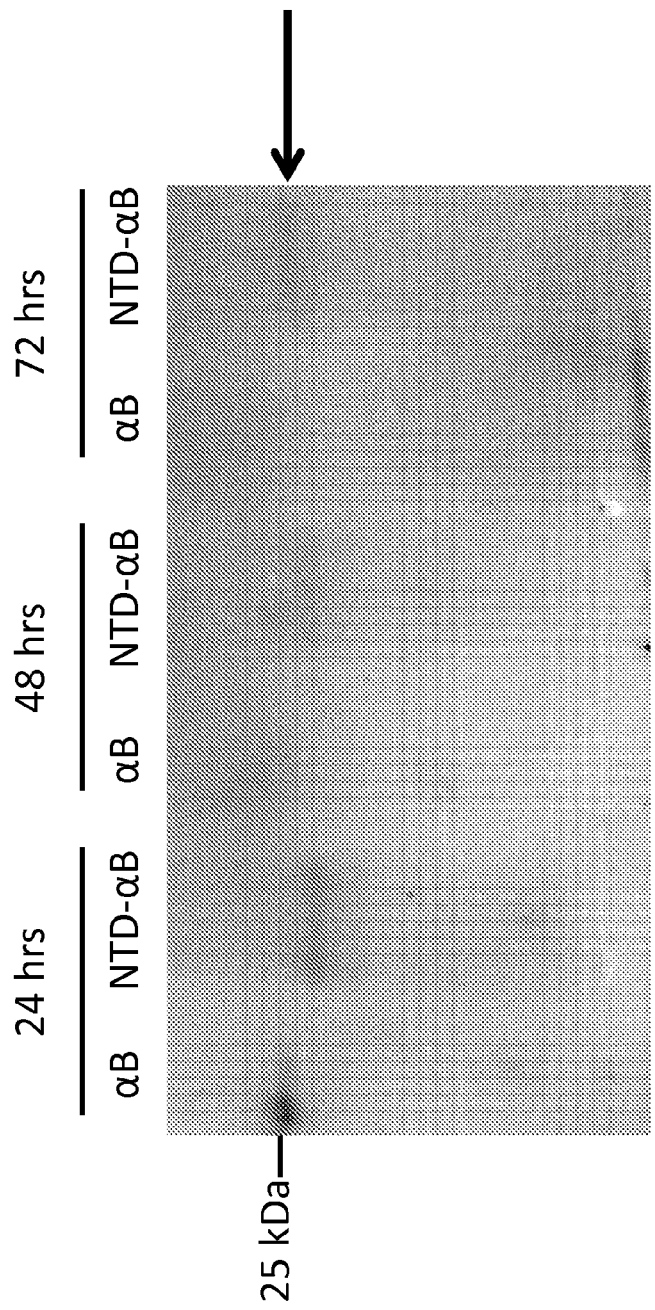
FIG. 7 presents SDS-PAGE and fluorescence detection of α-crystallin (native and tagged with NTD) extracted from tissue culture cells and demonstrates that NTD-tagged crystallin is stable inside cells.

Cells monitored for crystallin entry were extracted at various time points. Cell contents were examined by resolving proteins on SDS-PAGE, then measuring for the presence of Alexa-tagged crystallin using fluorescence. Data presented in FIG. 7 shows that most fluorescence signal comes from a protein band resolved by electrophoresis to correspond to the size expected for αB crystallin. This demonstrates that fluorescence signal observed in transduced cells arises from the intact αB crystallin rather than a degradation product of this material.

Example 4

This example illustrates the comparative efficiency of transduction and stabilization of NTD-αB crystallin and TAT-αB crystallin.

Figure 8:
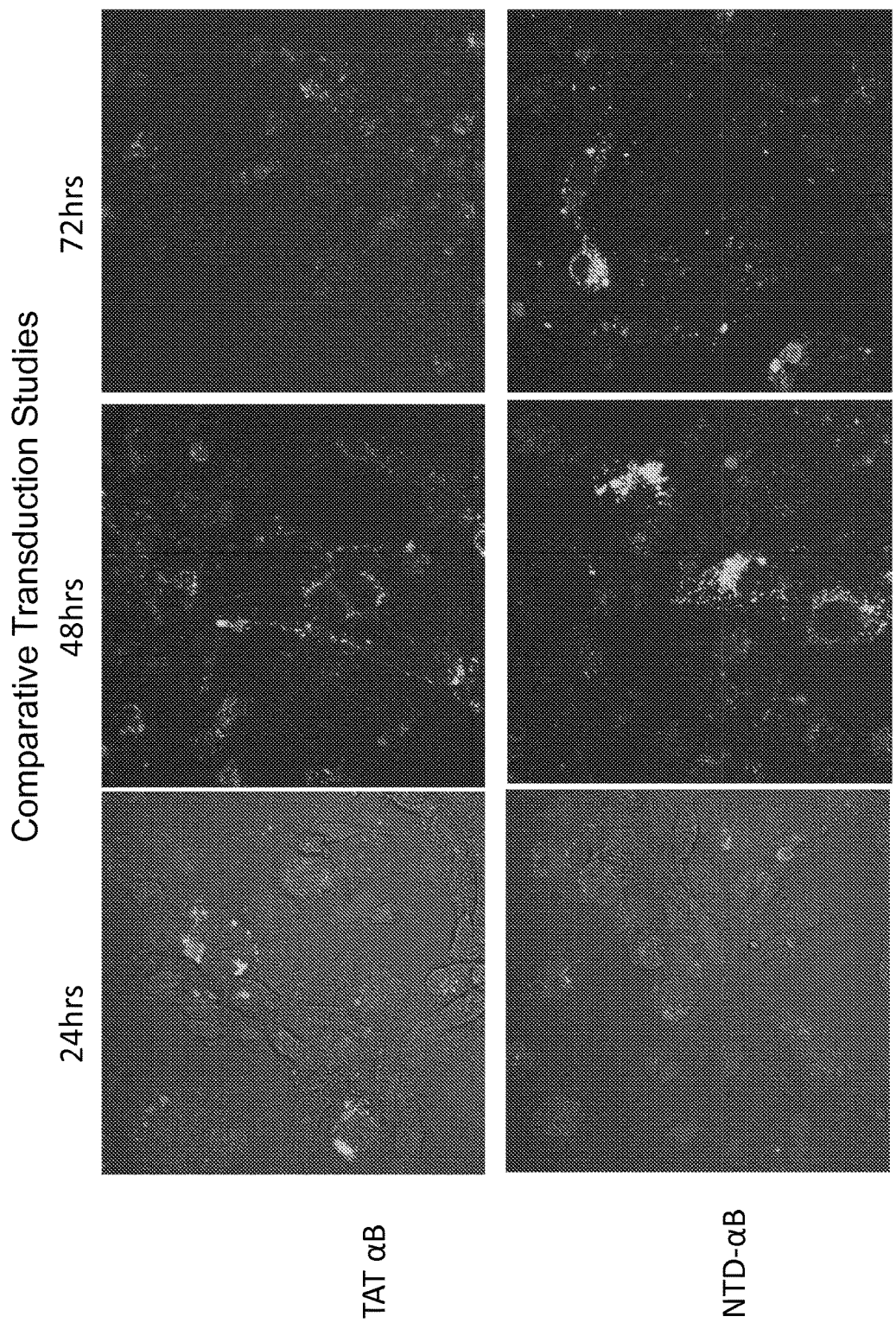
FIG. 8 shows the comparative efficiency of transduction and stabilization of αB crystallin fused to TAT or NTD sequences. Substantially stronger fluorescence signals in the NTD-αB treated cells, especially at 48 h and 72 h following treatment, indicate that the NTD-αB has stronger efficacy of transduction than TAT-αB.

As shown in FIG. 8, substantially stronger fluorescence signals were obtained in the NTD-αB crystallin treated cells, especially at 48 h and 72 h following treatment, as compared to TAT-αB crystallin treated cells. The TAT peptide (GRK-KRRQRRRPQ) is derived from the transactivator of transcription (TAT) of human immunodeficiency virus and is a cell-penetrating peptide. These data indicate that the NTD-αB crystallin has stronger efficacy of transduction than TAT-αB.

Figure 9:
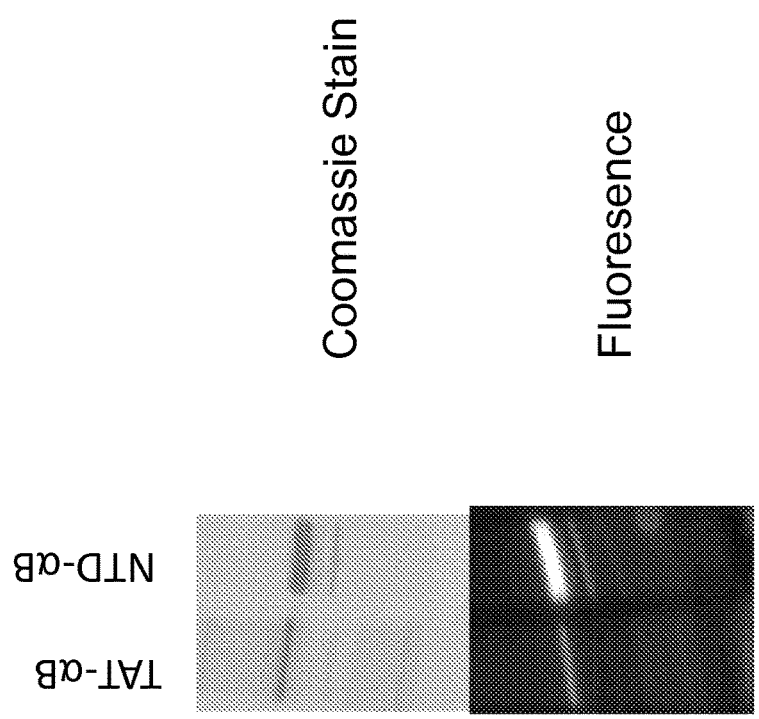
FIG. 9 shows SDS-PAGE and fluorescence analysis of purified αB crystallin fused to TAT or NTD sequences. These data demonstrate that NTD-αB crystallin fusion protein has a higher labelling efficiency than the TAT--αB crystallin fusion protein.

Further, FIG. 9 shows SDS-PAGE and fluorescence analysis of purified NTD- or TAT-αB crystallin proteins. These data demonstrate that NTD-αB crystallin fusion protein has a higher labelling efficiency than the TAT--αB crystallin fusion protein.

Example 5

This example illustrates that alpha crystallin is efficacious in preventing protein aggregation and promoting protein stabilization.

A tissue culture model system was tested using an endogenous target of alpha crystallin. Human gamma crystallin, either in its wild type form (γ-crystallin) or in an aggregation-prone mutant form (T5P γ-crystallin), was expressed as a fusion with green fluorescent protein (GFP). Strong fluorescence was observed in cells expressing the wild type γ-crystallin-GFP fusion protein; in contrast, cells expressing the T5P aggregation-prone mutant form of γ-crystallin-GFP fusion showed virtually no fluorescence. See FIG. 10, top two panels. However, treatment of these cells with alpha crystallin prevented the loss of fluorescence of the T5P-GFP fusion protein. See FIG. 10, bottom two panels. This indicates that alpha crystallin is efficacious in preventing protein aggregation and/or increasing stability of aggregation-prone proteins.

Similarly, as shown in FIG. 11, alpha crystallin prevented the loss of fluorescence of an aggregation-prone mutant of the protein rhodopsin (P23H rhodopsin). This mutation is the cause of the major form of retinitis pigmentosa in humans.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A composition comprising:
 a) a peptide comprising an amino acid sequence that is at least 80% identical to SEQ ID NO:1 (GSRVQIRCR-FRNSTR), and
 b) a therapeutic protein or a heat shock protein or a crystallin protein,
 wherein the peptide is linked to the N-terminus or C-terminus of the protein and the peptide facilitates or enhances the introduction of the protein or the nanoparticle into a cell.

2. A composition comprising:
 a) a peptide comprising an amino acid sequence that is at least 80% identical to SEQ ID NO:1 (GSRVQIRCR-FRNSTR), and
 b) a protein selected from the group consisting of an alpha crystalline protein and small heat shock proteins HSPB1, HSPB2, HSPB3, HSPB4, HSPB5, HSPB6, HSPB7, HSPB8, HSPB9 and HSPB10;
 wherein the peptide is linked to the protein and the peptide facilitates or enhances the introduction of the protein or the nanoparticle into a cell.

3. The composition of claim 2, wherein the protein is selected from the group consisting of αA-crystallin and αB-crystallin.

4. The composition of claim 3, wherein the peptide is linked to the N terminus of the protein.

5. The composition of claim 4, wherein the composition comprises a sequence that is at least 90% identical to SEQ ID NO:2 or SEQ ID NO:4.

6. An isolated nucleic acid molecule comprising a nucleic acid sequence encoding the composition of claim 1.

7. A recombinant nucleic acid molecule comprising the isolated nucleic acid molecule of claim 6.

8. The composition of claim 1 wherein the composition further comprises a pharmaceutically acceptable carrier.

9. A method of treating a disease in an individual, comprising administering to the individual the composition of claim 1 and wherein the disease is selected form the group consisting of an ocular disease, neurodegenerative disease, myopathy, asthma, and cancer.

10. The method of claim 9, wherein the ocular disease is selected from the group consisting of cataract, retinitis pigmentosa, retinopathy, age-related macular degeneration, uveitis, trauma and ischemia.

11. A method of treating a disease in an individual, comprising administering to the individual a composition comprising:
 a) a peptide comprising an amino acid sequence that is at least 80% identical to SEQ ID NO:1 (GSRVQIRCR-FRNSTR), and
 b) a therapeutic protein or a heat shock protein or a crystallin protein,
 wherein the peptide is linked to the N-terminus or C-terminus of the protein; the peptide facilitates or enhances the introduction of the protein into a cell, and wherein the protein provides a therapeutic benefit in the disease.

12. The composition of claim 2, wherein the peptide is linked to the N-terminus or the C-terminus of the heat shock protein.

13. The composition of claim 2, wherein the composition comprises a sequence that is at least 90% identical to SEQ ID NO:2 or SEQ ID NO:4.

14. The composition of claim 1, wherein the composition comprises a sequence that is at least 90% identical to SEQ ID NO:2 or SEQ ID NO:4.

* * * * *